(12) United States Patent
Patno et al.

(10) Patent No.: US 7,695,952 B2
(45) Date of Patent: Apr. 13, 2010

(54) DISPOSABLE SAMPLE PROCESSING MODULE FOR DETECTING NUCLEIC ACIDS

(75) Inventors: Tim Patno, Chicago, IL (US); Tom Westberg, Gurnee, IL (US)

(73) Assignee: Nanosphere, Inc., Northbrook, IL (US)

( * ) Notice: Subject to any disclaimer, the term of this patent is extended or adjusted under 35 U.S.C. 154(b) by 1262 days.

(21) Appl. No.: 10/982,292

(22) Filed: Nov. 5, 2004

(65) Prior Publication Data

US 2005/0170493 A1    Aug. 4, 2005

Related U.S. Application Data

(63) Continuation-in-part of application No. 10/703,368, filed on Nov. 7, 2003, now Pat. No. 7,396,677.

(60) Provisional application No. 60/589,768, filed on Jul. 21, 2004.

(51) Int. Cl.
*C12M 1/34* (2006.01)
*C12M 3/00* (2006.01)

(52) U.S. Cl. ............... 435/287.2; 435/287.1; 435/288.5

(58) Field of Classification Search ... 435/287.1–288.6, 435/6; 422/102
See application file for complete search history.

(56) References Cited

U.S. PATENT DOCUMENTS

| | | | | |
|---|---|---|---|---|
| 5,932,799 A * | 8/1999 | Moles | ........................ | 73/53.01 |
| 6,979,424 B2 * | 12/2005 | Northrup et al. | ............... | 422/50 |
| 2002/0123059 A1 * | 9/2002 | Ho | ................................. | 435/6 |
| 2003/0231989 A1 * | 12/2003 | Schleifer et al. | ............. | 422/102 |
| 2004/0043494 A1 * | 3/2004 | Amorese et al. | .............. | 436/37 |

* cited by examiner

*Primary Examiner*—Walter D Griffin
*Assistant Examiner*—Shanta G Doe
(74) *Attorney, Agent, or Firm*—Gregory T. Pletta

(57) ABSTRACT

A disposable sample processing module is provided for processing DNA or RNA samples. The module includes a hybridization chamber adapted to receive an oligonucleotide covalently bonded to an internal surface of the hybridization chamber. The module also include a sample well adapted to hold a DNA or RNA sample, said sample well being coupled to the hybridization chamber, a moveable valve plate disposed between the sample well and hybridization chamber, said moveable valve plate having a first position that allows transfer of the DNA or RNA sample from the sample well to the hybridization chamber and a second position that blocks transfer to the hybridization chamber and a manifold adapted to exchange fluids with the hybridization chamber to hybridize the DNA or RNA sample with the oligonucleotide, to wash the hybridized sample and to amplify the hybridized sample.

44 Claims, 9 Drawing Sheets

SAMPLE WELL: THERE ARE FOUR; THEY ARE THE INPUT INTO THE 4 HYBRIDIZATION CHAMBERS, 1000

WASTE PORTS: FOUR OF THEM; THEY ARE THE OUTPUTS FROM EACH OF THE HYBRIDIZATION CHAMBERS

SILICONE OVEREMOLDED ON TO METAL BLOCK; THE SILICONE IS SHOWN IN BLUE AND IS THE ONLY MATERIAL TO CONTACT THE SOLUTIONS AS PROTEINS AND DNA ARE UNAFFECTED BY SILICONE SURFACES

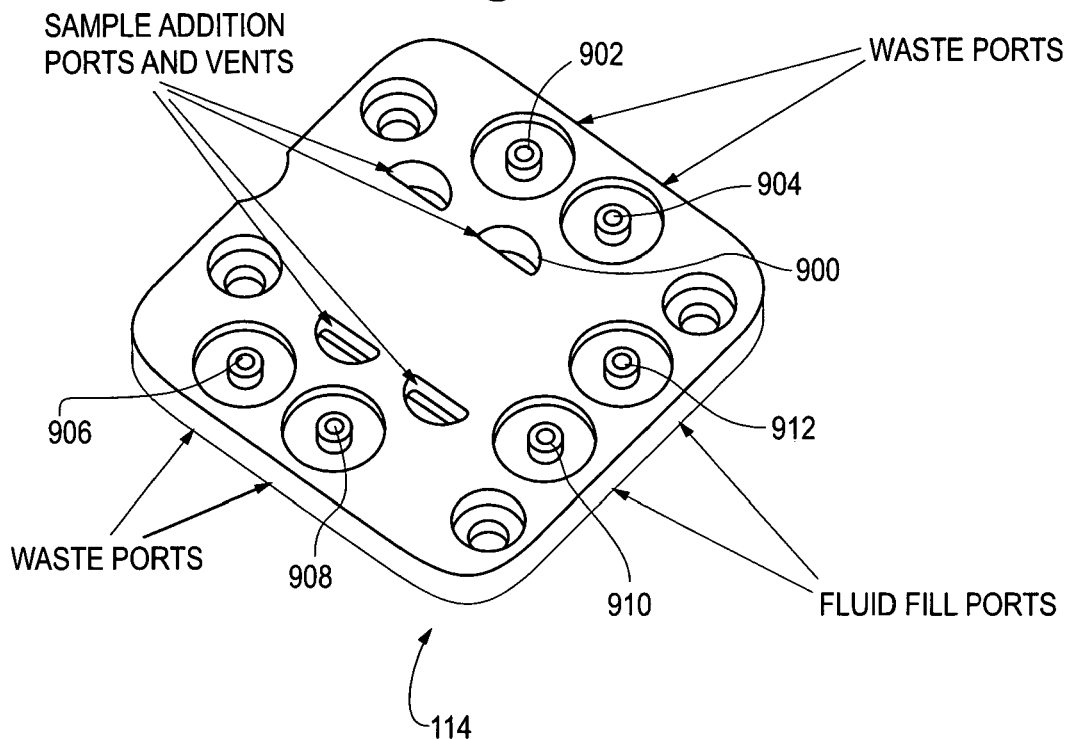
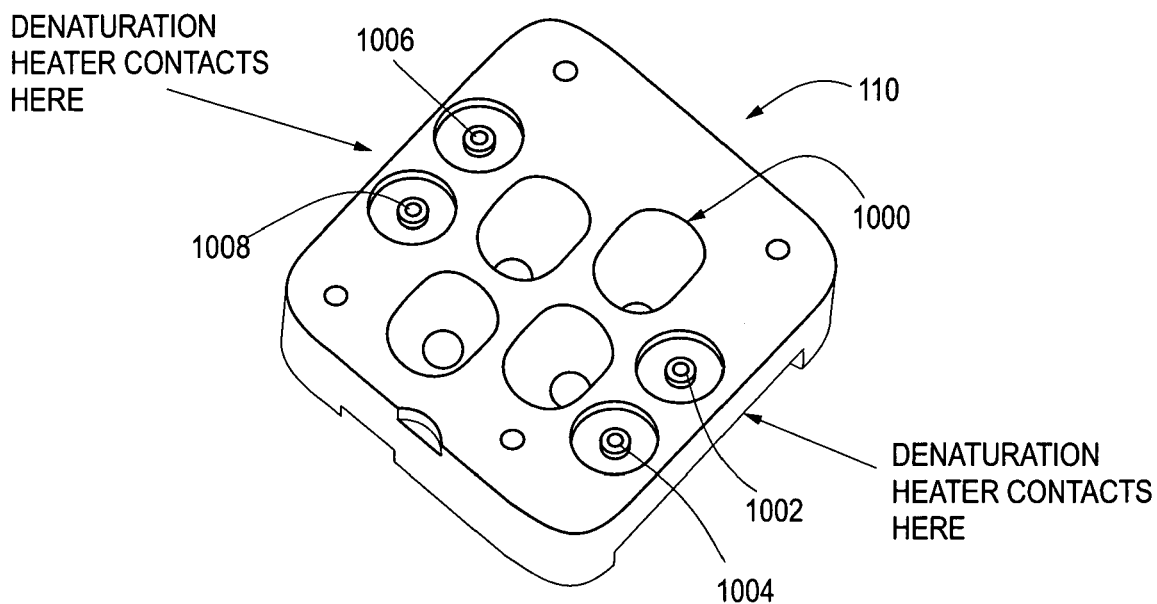

DISPOSABLE SAMPLE PROCESSING MODULE FOR DETECTING NUCLEIC ACIDS

This application is a Provisional of U.S. Patent Application No. 60/589,768 filed on Jul. 21, 2004 and is a continuation-in-part of U.S. patent application Ser. No. 10/703,368 filed on Nov. 7, 2003 which is now U.S. Pat. No. 7,396,677.

FIELD OF THE INVENTION

The field of the invention relates to biological testing and more particularly to detecting nucleic acids.

BACKGROUND OF THE INVENTION

Methods of detecting nucleic acids are generally known. In fact, there are a number of methods available for detecting specific nucleic acid sequences.

Known methods include those based upon electrophoresis, polymerase chain reaction (PCR) processes, various hybridization techniques, and a number of other techniques. While these methods are effective, they are all time consuming, costly and subject to significant human error.

For example, one manufacturer makes a microfluidics system that hybridizes a sample to a chip followed by staining of the chip. The hybridization process takes approximately 12 hours. Staining takes approximately 1.5 hours to complete.

Another supplier provides a system that relies upon a single nucleotide polymorphism (SNP) technique. This system uses a microchip for performing multiple assays. Probes are added to a cartridge and the particles move based on charge in an electric field. A detection system may be used for analyzing the cartridges after hybridization with the sample DNA.

Still another supplier provides a device called a Lightcycler that combines PCR amplification and DNA detection into one process. The Lightcycler can use one of two processes for detection. The first process relies upon PCR and hybridization. The second process relies upon PCR and dye and melting curve analysis.

The development of reliable methods for detecting and sequencing nucleic acids is critical to the diagnosis of genetic, bacterial and viral diseases. Because of the importance of health care and disease prevention, a need exists for quicker and cheaper methods of identifying nucleic acids.

SUMMARY

A disposable sample processing module is provided for processing DNA or RNA samples. The module includes a hybridization chamber adapted to receive an oligonucleotide covalently bonded to an internal surface of the hybridization chamber. The module also includes a sample well adapted to hold a DNA or RNA sample, said sample well being coupled to the hybridization chamber, and a moveable valve plate disposed between the sample well and hybridization chamber, said moveable valve plate having a first position that allows transfer of the DNA or RNA sample from the sample well to the hybridization chamber and a second position that blocks transfer to the hybridization chamber. The module also includes a manifold adapted to exchange fluids with the hybridization chamber to hybridize the DNA or RNA sample with the oligonucleotide, to wash the hybridized sample and to amplify the hybridized sample.

BRIEF DESCRIPTION OF THE DRAWINGS

FIG. 9 is a top, perspective view of the pumping plate of FIG. 3;

FIG. 10 is a top, perspective view of the sample well of FIG. 3;

DETAILED DESCRIPTION OF AN ILLUSTRATED EMBODIMENT

Figure 1:
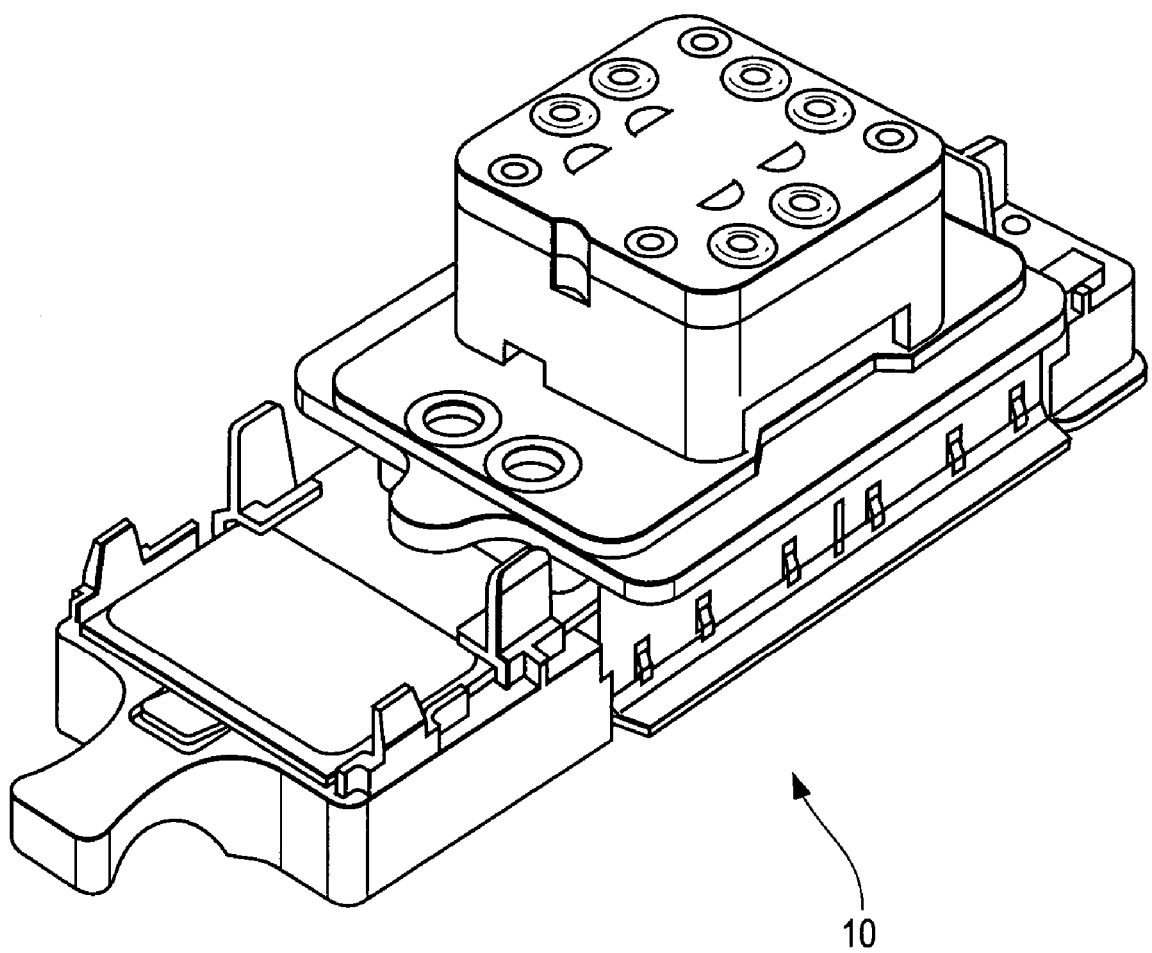
FIG. 1 is a perspective view of a disposable sample processing module under an illustrated embodiment of the invention.

FIG. 1 depicts a disposable sample processing module 10 for detecting nucleic acids generally in accordance with an illustrated embodiment of the invention. The module 10 may generally be used in place of similar modules (referred to as hybridization units) described in parent U.S. patent application Ser. No. 10/703,368 filed on Nov. 7, 2003 (incorporated herein by reference).

Figure 2:
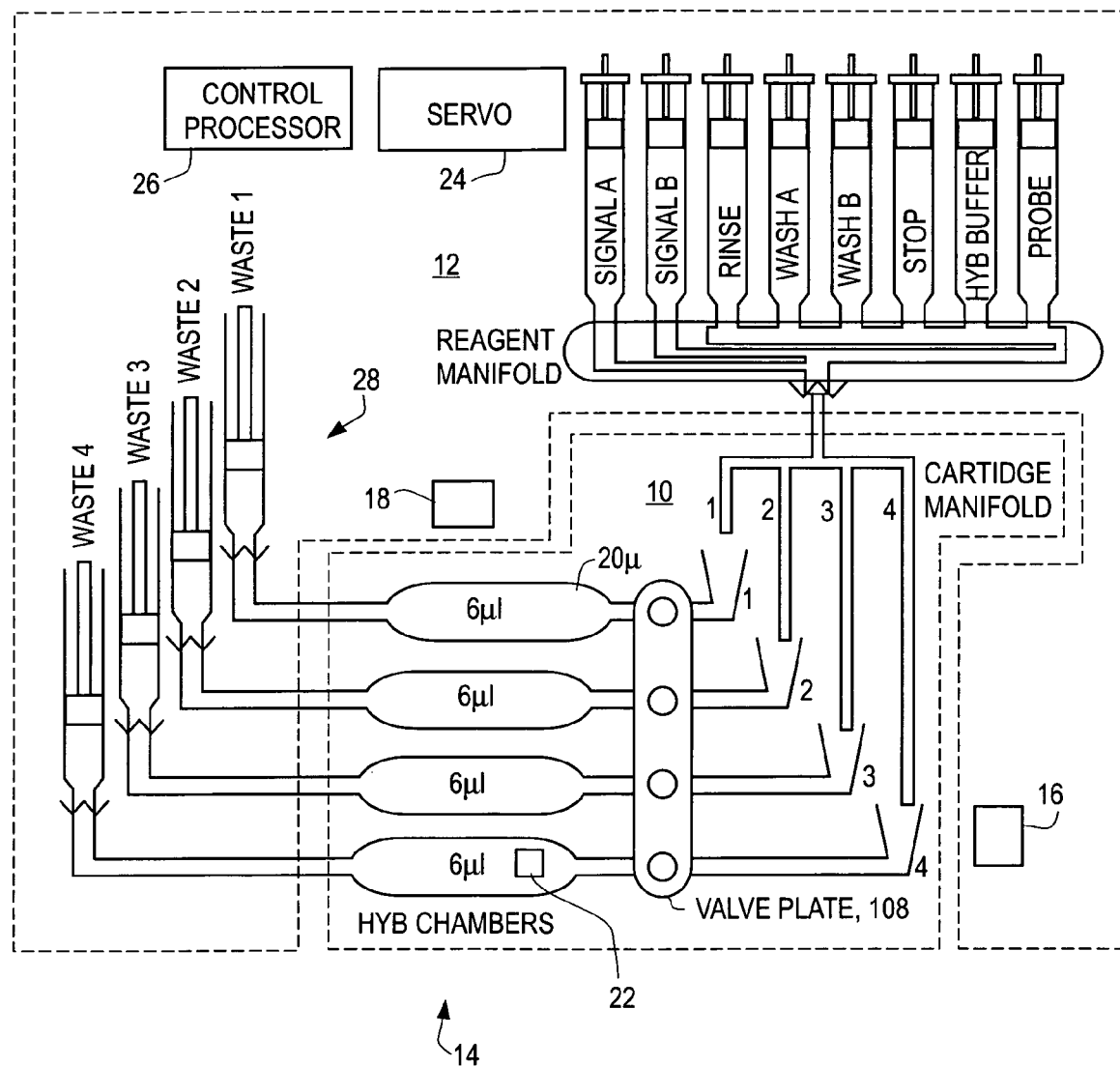
FIG. 2 is a block diagram of the processing module of FIG. 1 in a context of use.

FIG. 2 is a block diagram that shows a simplified version of the nucleic acid detection system of the parent application. The system 14 of FIG. 2 may include a processing unit 12 that accepts the disposable sample processing module 10. Within the processing unit 12, the sample module 10 may be subjected to a number of processing steps described in more detail below and in the parent application.

The processing system 14 may be used for the detection of any of a number of predetermined target nucleic acids. In fact, any type of nucleic acid may be detected, and the methods may be used for the diagnosis of disease and in sequencing of nucleic acids. Examples of nucleic acids that can be detected by the methods of the invention include genes (e.g., a gene associated with a particular disease), viral RNA and DNA, bacterial DNA, fungal DNA, cDNA, mRNA, RNA and DNA fragments, oligonucleotides, synthetic oligonucleotides, modified oligonucleotides, single-stranded and double-stranded nucleic acids, natural and synthetic nucleic acids, etc. Examples of the uses of the methods of detecting nucleic acids include: the diagnosis and/or monitoring of viral diseases (e.g., human immunodeficiency virus, hepatitis viruses, herpes viruses, cytomegalovirus, and Epstein-Barr virus), bacterial diseases (e.g., tuberculosis, Lyme disease, *H. pylori, Escherichia coli* infections, Legionella infections Mycoplasma infections, Salmonella infections), sexually transmitted diseases (e.g., gonorrhea), inherited disorders (e.g., cystic fibrosis, Duchene muscular dystrophy, phenylketonuria, sickle cell anemia), and cancers (e.g., genes associated with the development of cancer); in forensics; in DNA sequencing; for paternity testing; for cell line authentication; for monitoring gene therapy; and for many other purposes.

Figure 3:
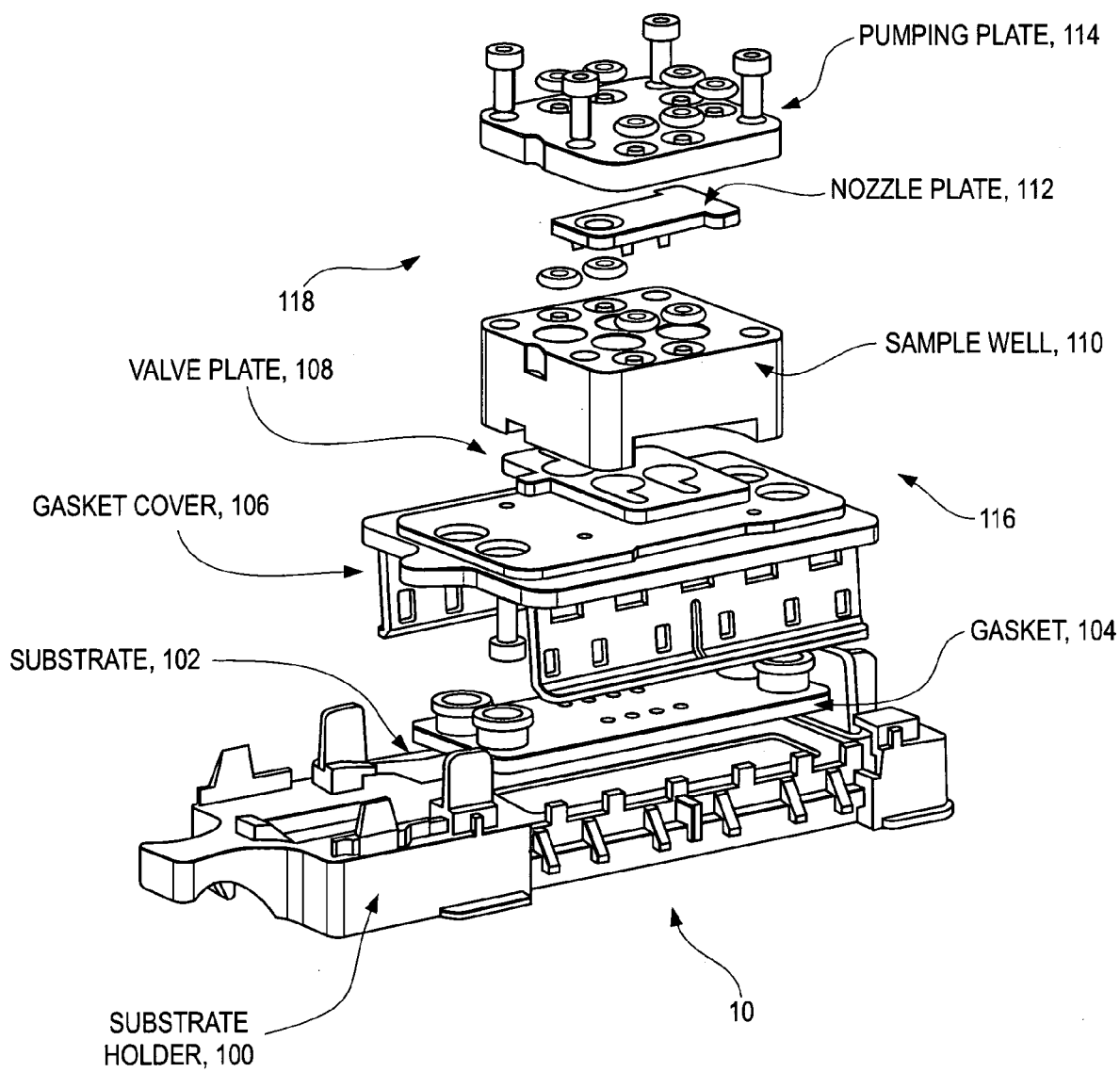
FIG. 3 is an exploded view of the module of FIG. 1.

FIG. 3 is an exploded view of the sample processing module 10. As shown, the sample processing module 10 may include a substrate holder 100, a substrate 102, a gasket 104 and a gasket cover 106. Attached to the gasket cover 106 may be a module manifold 116 and a sample well assembly 118.

The module manifold 116 may include portions of a valve plate 108, a sample well 110, a nozzle plate 112 and a pumping plate 114. The sample well assembly 118 may include portions of the sample well 110 and the pumping plate 114.

Figure 4:
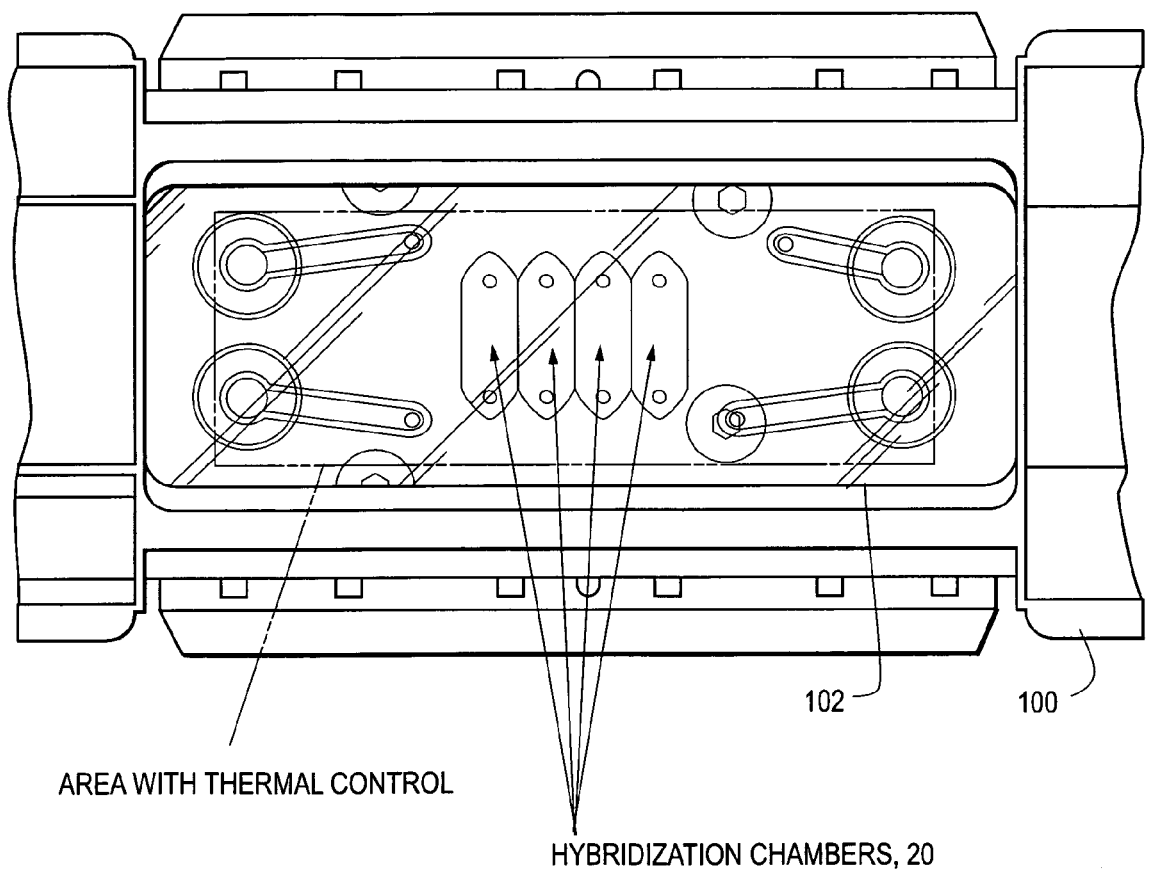
FIG. 4 is a bottom view of the module of FIG. 1.
Figure 5A:
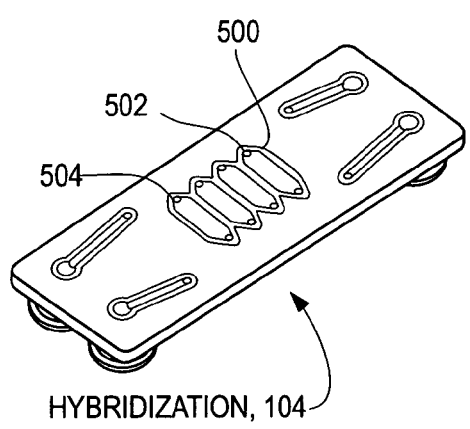
FIGS. 5a-b are top and bottom views of the gasket of FIG. 3.
Figure 5B:
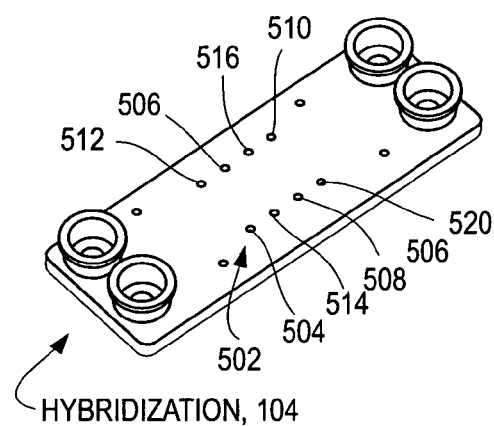
Figure 6A:
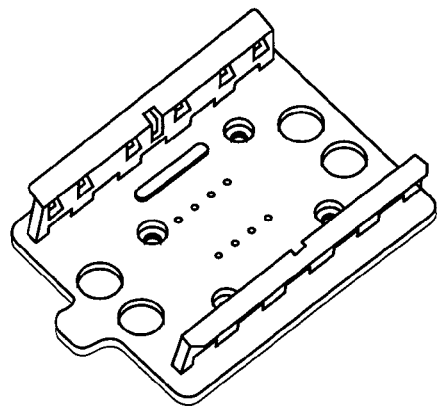
FIGS. 6a-b are top and bottom views of the gasket cover of FIG. 3.
Figure 6B:
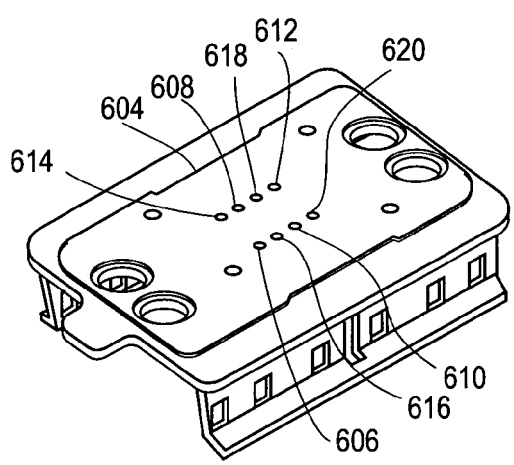

The substrate 102 may be formed from silicon glass. The substrate holder 100 may have an unobstructed center section (as shown in the bottom view of the module 10 shown in FIG. 4) to allow a heating/cooling module 18 (FIG. 2) to be placed against a lower surface of the substrate 102. A thermocouple may be use to accurately control the temperature of the hybridization chambers 20 in a range of from 10-70° C.+/−1° C. In general, the substrate holder 100 and substrate 102 may be fabricated generally as shown in the parent application.

In general, the temperature of the hybridization chambers 20 may be controlled during the sample hybridization and during all subsequent phases. The temperature can be the same for all phases (hybridization, wash, signal amplification, etc.), or varied among the processing phases.

FIGS. 5*a-b* and 6*a-b* show top and bottom views of the gasket 104 and gasket cover 106. In general, the gasket 104 may be made of silicone. The gasket cover 106 may be made of a polycarbonate to withstand the heat applied to the sample module 10.

The gasket 104 may be provided with a set of oblong shaped, raised ridges 500 (FIG. 5*a*) that define the outlines of a set of hybridization chambers 20. Along each marginal end of each oblong shape is an aperture 502. A complementary set of apertures 604 is also shown passing through the gasket cover 106.

In use, the gasket 104 is placed on the substrate 102 with the ridges 500 in direct contact with the substrate 102. The volumes between the substrate 102 and gasket 104 surrounded by the ridges 500 define the hybridization chambers 20.

The hybridization chamber 20 may be of any appropriate size (e.g., 5-20 microliter). The volume of the hybridization chamber 20 is dependent upon the area needed to accommodate the number of required target sites on the substrate 102.

Figure 7A:
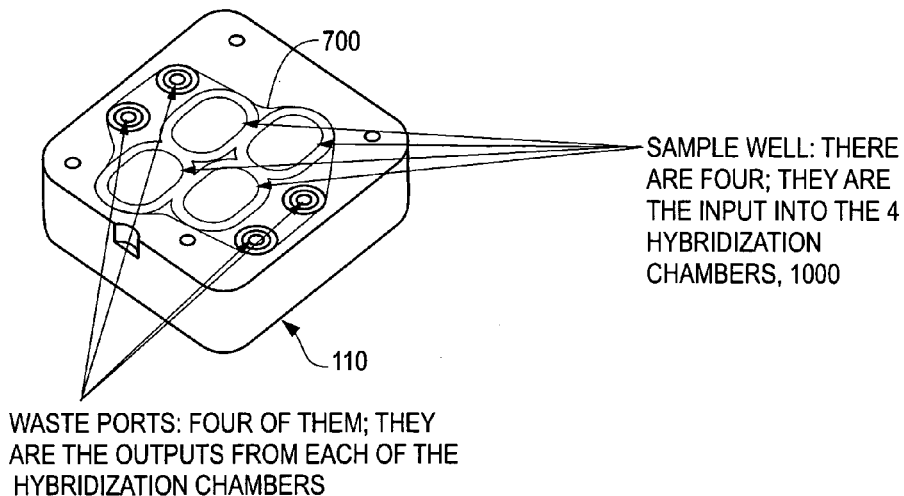
FIGS. 7a-b are top and bottom views of the sample well of FIG. 3.

Disposed above the gasket cover 106 is the manifold 116 and sample well assemblies 118. As shown in FIGS. 7*a* and 10, the sample well body 110 may be provided with four sample wells 1000. While four sample wells 1000 are shown, it should be understood that a greater or lesser number of sample wells 1000 could be provided.

Figure 7B:
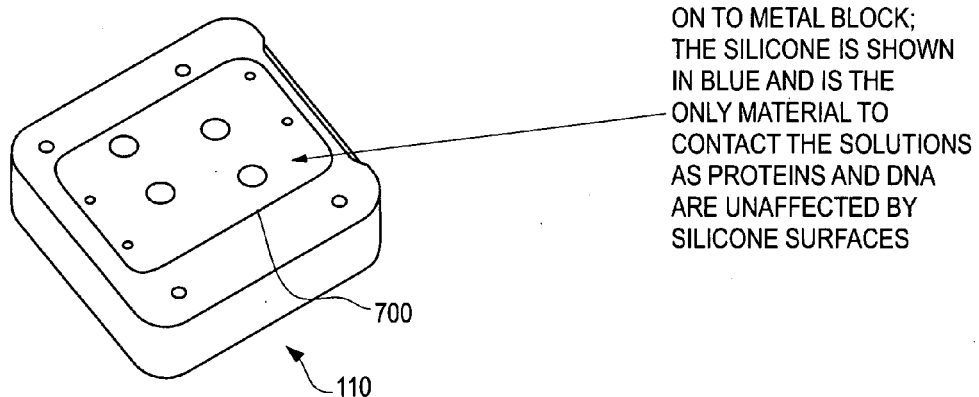

A set of sample apertures 900 (FIG. 9) are provided in the top surface of the pumping plate 114 through which a technician may introduce the DNA or RNA samples into one or more of the sample wells 1000 (FIGS. 7*a-b*, 10) using a micropipette or otherwise.

The sample well body 110 may be fabricated of a material that has good heat conduction (e.g., aluminum). To avoid interaction of the DNA or RNA samples with the sample well body 110 (e.g., sticking), the sample contact areas may be overmolded with a layer 700 of silicone. The layer 700 is relatively thin (e.g., 1 mm) so as to not inhibit heat transfer to the sample.

When the samples are being added to the module 10, the bottom of each sample well 1000 is closed via the valve plate 108. FIG. 8*b* show a top view of the valve plate 108.

Figure 8A:
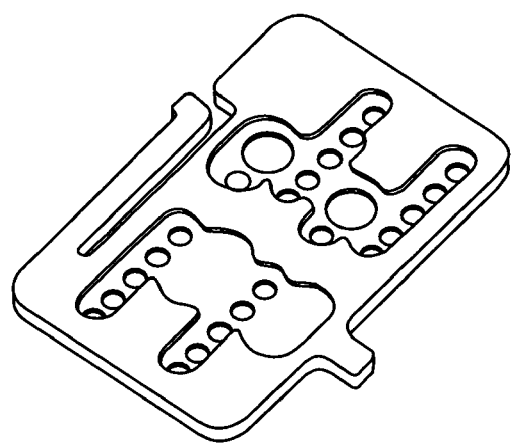
FIGS. 8a-b are top and bottom views of the valve plate of FIG. 3 in both a semi-finished and finished state.
Figure 8B:
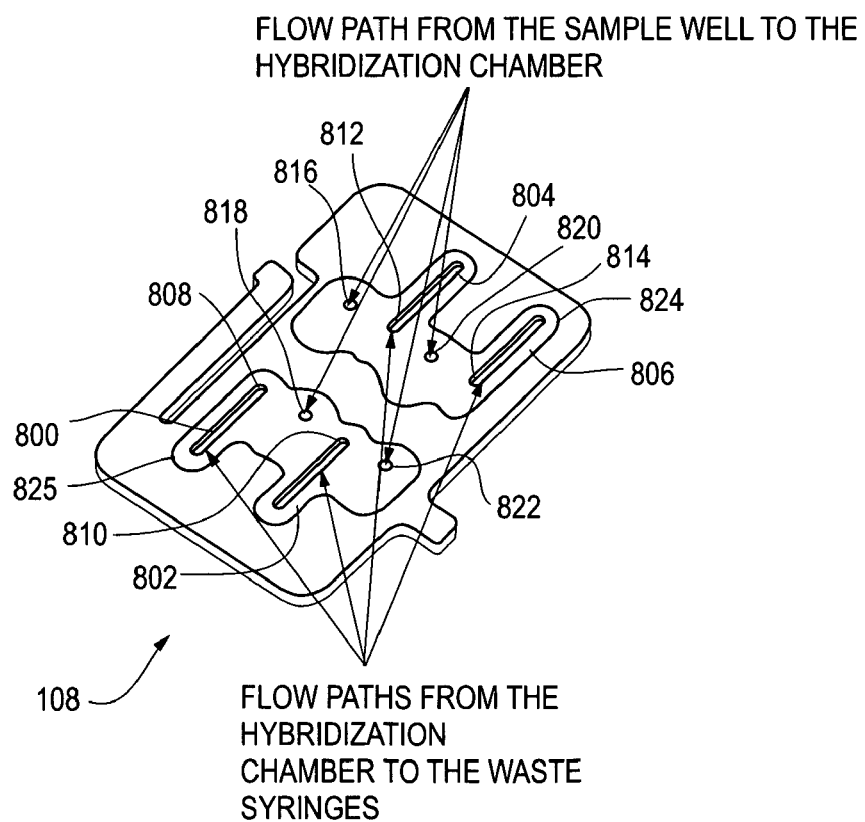

The valve plate 108 may be fabricated of a polycarbonate (as shown in FIG. 8*a*) with silicone overmolded layers 824, 825. A set of channels 800, 802, 804, 806 may be formed in the silicone as part of the overmolding process.

The valve plate 108 has two positions. In one position, the valve plate 108 separates and isolates a sample well 1000 from its respective hybridization chamber 20. In another position, the sample wells 1000 and respective hybridization chambers 20 are connected via a set of respective apertures and passageways through the valve plate 108.

When the samples are being pipetted (loaded) into the module 10, the valve plate 108 is in a closed position to prevent the sample from entering the hybridization chamber 20. Once the module 10 is inserted into the processing unit 12, a servo 24 (FIG. 2) within the processing unit 12 may engage and move the valve plate to the open position, as discussed below.

Turning next to the manifold 116, a number of passageways connect the hybridization chambers 20 or sample wells 1000 and the pumping ports 902, 904, 906, 908, 910, 912 (FIG. 9). A first set of pumping (fluid fill) ports 910, 912 may be used to introduce fluids to the hybridization chambers 20 via the sample wells 1000. A second set of pumping (waste) ports 902, 904, 906, 908 may be used to draw waste products directly from the hybridization chambers 20 via passageways through the valve plate 108, through a set of peripheral passageways within the sample well 110 and pumping plate 114.

With regard to the fill ports 910, 912, a number of features may be provided to ensure a complete mixing of fluid components. For example, a microfluidics mixing chamber 1102 (FIG. 11) and set of nozzles 1200 (FIG. 12) may be provided on a nozzle plate 112 to achieve this objective. In this regard, FIG. 9 shows a top view of the pumping plate 114 and FIG. 12 shows a bottom view of the pumping plate 114. The nozzle plate 112 may be attached to the bottom of the pumping plate 114 as shown in FIG. 12 via adhesives or a laser welding process.

Figure 11:
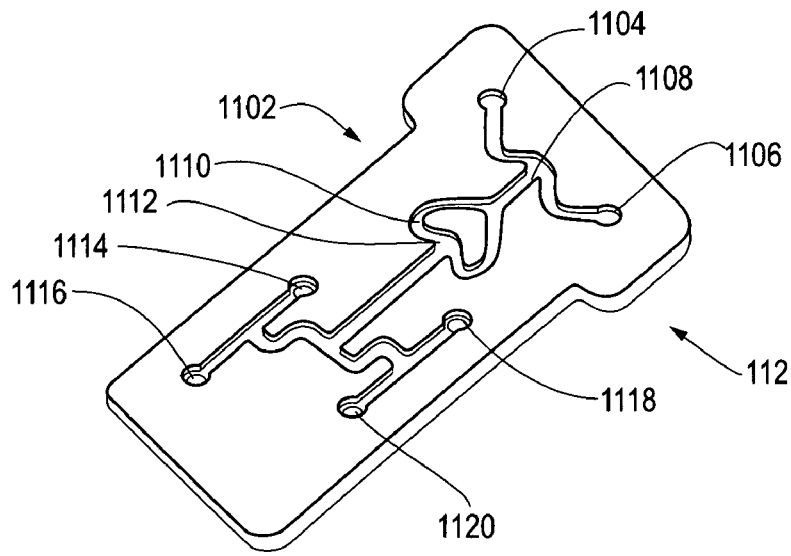
FIG. 11 is a top, perspective view of the nozzle plate of FIG. 3.
Figure 12:
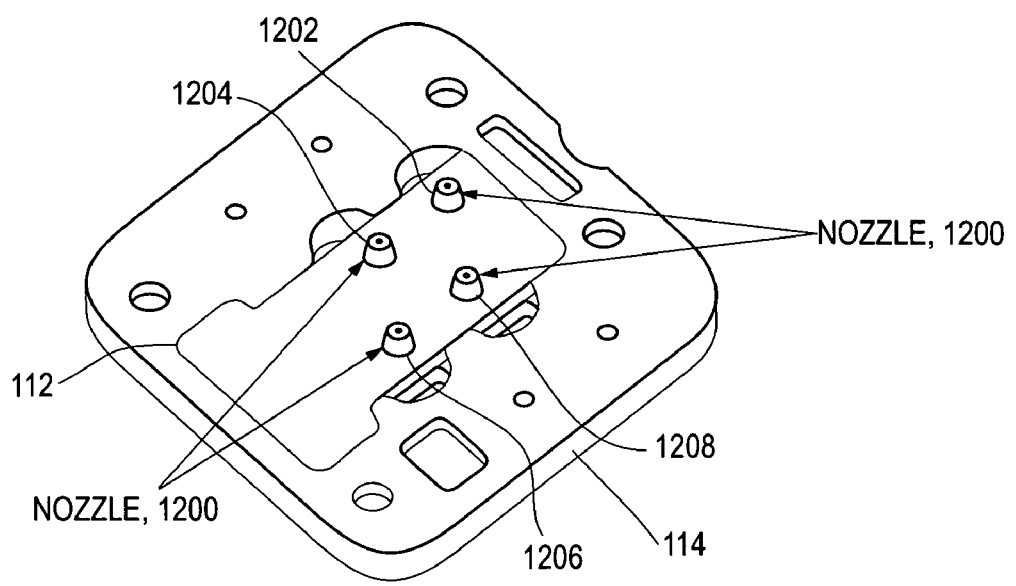
FIG. 12 is a bottom, perspective view of the assembled pumping plate and nozzle plate.

As shown in FIG. 11, a set of channels are provided within the nozzle plate 112 to connect the fill ports 910, 912 to the nozzles 1200 (FIG. 12). The fill port 902 may connect (via an aperture through the pumping plate 114 and nozzle plate 112) to a first branch 1104 of the channels and a second fill port 904 may connect to a second branch 1106 of the channels. When fluids are simultaneously introduced into both fill ports, the fluids impinge from opposite directions within a first mixing area 1108. The mixed fluids are then divided by a divider 1110 before impinging within a second mixing area 1112.

The mixed fluids may then be distributed through four distribution branches. A first aperture 1116 through the nozzle plate 112 at the end of a first branch may connect to a first nozzle 1202, a second aperture 1114 may connect to a second nozzle 1204, a third aperture 1120 may connect to a third nozzle 1208 and a fourth aperture 1118 may connect to a fourth nozzle 1206.

The nozzles 1200 function to spray the mixed fluids into the respective sample wells 1000. The nozzles are accurately formed via an appropriate process (e.g., laser drilling) to an appropriate diameter (e.g., 200 microns). Equal distribution of the mixed fluids is ensured by a substantially equal nozzle diameter and proper flushing of the sample wells is ensured by a relatively large flow rate (e.g., 200 microliters per second or greater). With a flow of 300 microliters it has been found that the fluid can be distributed with less than 10 microliter variation among the nozzles.

The waste ports 902, 904, 906, 908 will be considered next. In this regard, apertures through the pumping plate 114 connect the waste ports 902, 904, 906, 908 (FIG. 9) to respective passageways 1002, 1004, 1006, 1008 (FIG. 10) that extend downwardly through the sample well 110. The passageways 1002, 1004, 1006, 1008 terminate within the channels 800, 802, 804, 806 of the valve plate 108 (FIG. 8*b*). The channels 800, 802, 804, 806, in turn, are provided with respective apertures 808, 810, 812, 814.

A corresponding set of apertures 606, 608, 810, 812 are provided through the gasket cover and a matching set of apertures 506, 508, 510, 512 are provided through the gasket 104. The combination of apertures and passageways functions to connect one end of each hybridization zone 20 to a respective waste port 902, 904, 906, 908.

The second end of each hybridization zone 20 may be connected to a sample well 1000 in a similar manner. For example, the bottom of each sample well 1000 is in direct contact with the top of the valve plate 108. Apertures 816, 818, 820, 822 may be positioned directly beneath a respective sample well 1000 when the valve plate 108 is in the "ON" position. A corresponding set of apertures 512, 514, 516, 518 in the gasket 104 and set of apertures 614, 616, 618, 620 in the gasket cover 106 function to complete the passageway between a sample well 1000 and a respective, second end of the hybridization chamber 20.

In use, a target DNA or RNA sample may be hybridized with an oligonucleotide within one or more of the hybridization chambers 20. Detection of the hybridized materials may be amplified by an autometallographic process where metal ions such as from silver nitrate are reduced to silver atoms that preferentially bind to nanoparticles within an oligonucleotide.

In preparation for testing for a particular nucleic acid, a first oligonucleotide or first group of oligonucleotides 22 with a first predetermined genetic sequence may be disposed on the substrate 102 (FIG. 3) within one or more of the hybridization zones 20. The first oligonucleotides 22 may have a genetic sequence that is complementary to a first portion of the genetic sequence of the predetermined target nucleic acid.

Probes may be constructed of nanoparticles with one or more strands of second oligonucleotides of a second predetermined genetic sequence attached to the nanoparticles. Nanoparticles useful in the practice of the invention may include metal (e.g., gold, silver, copper, and platinum), semiconductor (e.g., CdSe, CdS, and CdS or CdSe coated with ZnS) and magnetic (e.g., ferromagnetite) colloidal materials. Other nanoparticles useful in the practice of the invention include ZnS, ZnO, $TiO_2$, AgI, AgBr, $HgI_2$, PbS, PbSe, ZnTe, CdTe, $In_2S_3$, $Cd_3P_2$, $Cd_3As_2$, InAs, and GaAs. The size of the nanoparticles is preferably from about 5 nm to about 150 nm (mean diameter), more preferably from about 5 to about 50 nm, most preferably from about 10 to about 30 nm.

The nanoparticles, the second oligonucleotides or both are functionalized in order to attach the oligonucleotides to the nanoparticles. Such methods are known in the art. For instance, oligonucleotides functionalized with alkanethiols at their 3'-termini or 5'-termini readily attach to gold nanoparticles.

The second oligonucleotides may have a sequence that is complementary to a second portion of the genetic sequence of the predetermined target nucleic acid. Preparation of the first and second oligonucleotides and attachment to the respective particles and substrate may be accomplished generally as described in U.S. Pat. No. 6,417,340 assigned to the assignee of the present invention and incorporated herein by reference.

In general, the test sample (that may or may not contain the predetermined target nucleic acid) and a hybridization fluid may be mixed in a sample well. A probe may be added to the sample well 1000 or may be added later. The mixture may be denatured before the mixture enters the hybridization chamber. Denaturing may be accomplished using any known process (e.g., heat, chemical, etc.).

Before addition of the sample, it may be assumed that the valve plate 108 is in its closed position to prevent entry of the sample into the hybridization chamber 20. The valve 108 is closed to prevent interaction of the sample with the first oligonucleotide before denaturization is complete.

Once the sample processing module 10 has been prepared by a technician, the module 10 may be inserted into the processing system 12. Upon insertion of the module 10, a set of sample heaters 16 may be disposed against one or both sides of the sample well 108 to denature the sample. A second set of heaters 18 may also be disposed against the bottom of the substrate 102 to heat or cool the hybridization chambers 20. Thermocouples within the processing system 12 may be used to detect and control the temperatures.

The temperature of the contents of the sample well 1000 and the hybridization chamber 20 may be carefully controlled to ensure a successful test. The contents of the sample well 1000 may be heated to 95° C. for denaturation of the biomolecules (e.g., DNA). Heating of up to 130° C. may be provided for concentration of sample fluids via evaporation. The temperature control may be 95° C.+/−5° C. and 130° C.+/−10° C.

Once the temperature of the module 10 has been stabilized, the stepper motor 24 may be activated by a controller 26 to open the valve plate 108. A set of waste pumps 28 may be activated to pull the mixture into the hybridization chamber 20. A shuttling motion may be used as described in parent application Ser. No. 10/703,368 to facilitate sample hybridization.

Following hybridization, one or more washing steps may occur with wash solutions. If a probe was not included in the sample, then a probe solution can be added following the first wash and a probe hybridization may occur over a predetermined time period determined by the controller 26. The probe hybridization may be of a duration of 5 to 30 minutes depending upon the application. Another series of washes can be performed following the probe hybridization.

One or more solutions can be added during each processing phase. Typically one solution is added except for during probe hybridization and signal amplification when two solutions may be added in parallel. When two solutions are added, the fluid mixer 1102 in the sample module 10 mixes the fluids.

Two common fluid fill ports 910, 912 may be used to provide the fluid to the four channels. Each sample well 1000, which acts as a repository for the fluids is vented. Once the fluids are added to the sample well, they are pulled through the hybridization chamber 20 via a pump 28 that interfaces uniquely with a single hybridization chamber 20. Cross-contamination of samples is mitigated with the independent flow path design.

A specific embodiment of a disposable sample processing module has been described for the purpose of illustrating the manner in which the invention is made and used. It should be understood that the implementation of other variations and modifications of the invention and its various aspects will be apparent to one skilled in the art, and that the invention is not limited by the specific embodiments described. Therefore, it is contemplated to cover the present invention and any and all modifications, variations, or equivalents that fall within the true spirit and scope of the basic underlying principles disclosed and claimed herein.

The invention claimed is:

1. A disposable sample processing module for processing DNA or RNA samples, such module comprising:

a hybridization chamber adapted to receive an oligonucleotide covalently bonded to an internal surface of the hybridization chamber;

a sample well adapted to hold a DNA or RNA sample, said sample well being coupled to the hybridization chamber;

a moveable valve plate disposed between the sample well and hybridization chamber, where a bottom of the sample well is in direct contact with a top of the valve plate, the valve plate having a preexisting channel extending through the moveable valve plate, said moveable valve plate having a first position relative to the sample well and hybridization chamber where the channel of the valve plate completes a passageway between the hybridization chamber and sample well and that allows transfer of the DNA or RNA sample from the sample well to the hybridization chamber and a second position relative to the sample well and hybridization chamber where a body of the valve plate blocks the passageway to prevent transfer to the hybridization chamber; and a manifold adapted to exchange fluids with the hybridization chamber to hybridize the DNA or RNA sample with the oligonucleotide, to wash the hybridized sample and to amplify the hybridized sample.

2. The disposable sample processing module as in claim 1 further comprising a plurality of hybridization chambers and respective sample wells, each allowing transfer of fluids via the moveable valve plate and manifold.

3. The disposable sample processing module as in claim 2 wherein the plurality of hybridization chambers further comprises a substrate.

4. The disposable sample processing module as in claim 3 further comprising a flexible gasket and gasket cover combination disposed against the substrate, said gasket disposed between the substrate and gasket cover and forming the plurality of hybridization chambers between the gasket and substrate.

5. The disposable sample processing module as in claim 4 further comprising a sample well assembly disposed adjacent the gasket cover on a side of the gasket cover that is opposite the substrate, said sample well assembly further comprising the plurality of sample wells that receive one or more DNA or RNA samples and that communicate the DNA or RNA samples to the respective hybridization chambers through the gasket cover.

6. The disposable sample processing module as in claim 4 wherein the substrate further comprises a silicon glass.

7. The disposable sample processing module as in claim 6 wherein the silicon glass substrate is adapted to contact an external heating or cooling source.

8. The disposable sample processing module as in claim 5 wherein the flexible gasket further comprises silicone.

9. The disposable sample processing module as in claim 5 wherein at least some hybridization chambers of the plurality of hybridization chambers further comprise a volume of from 5 to 20 microliters.

10. The disposable sample processing module as in claim 5 wherein at least some hybridization chambers of the plurality of hybridization chambers further comprise an oligonucleotide covalently bonded to an internal surface.

11. The disposable sample processing module as in claim 5 wherein the valve plate further comprises polycarbonate.

12. The disposable sample processing module as in claim 11 wherein the polycarbonate valve plate further comprises an overmolded inert layer of silicone where the DNA or RNA samples contact the valve plate.

13. The disposable sample processing module as in claim 5 further comprising a pumping plate disposed adjacent the sample well on a side of the sample well that is opposite the gasket cover, said pumping plate further comprising a plurality of pumping ports that communicate fluids into and out of the processing module.

14. The disposable sample processing module as in claim 13 wherein the pumping plate further comprises polycarbonate.

15. The disposable sample processing module as in claim 13 wherein the plurality of pumping ports further comprise at least one waste port and a waste channel that connects the waste port with a respective hybridization chamber of the plurality of hybridization chambers.

16. The disposable sample processing module as in claim 15 wherein the waste channel further comprises a passageway through the valve plate that is blocked when the valve plate is in the second position.

17. The disposable sample processing module as in claim 15 wherein the plurality of pumping ports further comprise at least a first fluid fill port that directs fluid to each sample well of the plurality of sample wells.

18. The disposable sample processing module as in claim 17 further comprising a nozzle plate disposed between the pumping plate and the sample well, said nozzle plate having a plurality of nozzles that correspond to the plurality of sample wells and wherein a fluid introduced through the pumping nozzle is sprayed into a sample well of the plurality of sample wells through a respective nozzle of the plurality of nozzles.

19. The disposable sample processing module as in claim 18 wherein each nozzle of the plurality of nozzles further comprises a diameter of approximately 200 microns.

20. The disposable sample processing module as in claim 19 wherein the fluid sprayed through the nozzles further comprises approximately 200 microliters per second.

21. The disposable sample processing module as in claim 18 further comprising a second fluid fill port of the plurality of pumping ports, said second fluid fill port communicating with said first fluid fill port.

22. The disposable sample processing module as in claim 21 wherein the nozzle plate further comprising a microfluidics mixing chamber that mixes fluids from the first and second fluid fill ports before the mixed fluids are introduced into the plurality of sample wells.

23. The disposable sample processing module as in claim 5 wherein the sample well assembly further comprises a metal body adapted to interact with an external heater to denature the DNA or RNA samples.

24. The disposable sample processing module as in claim 23 wherein the metal body further comprises a relatively thin coating of silicone within each sample well of the plurality of sample wells to isolate the DNA or RNA samples from the metal body.

25. A disposable sample processing module for processing DNA or RNA samples, such module comprising:

a substrate;

a flexible gasket and gasket cover combination disposed against the substrate, said gasket disposed between the substrate and gasket cover and forming a plurality of hybridization chambers between the gasket and substrate;

a sample well assembly disposed adjacent the gasket cover on a side of the gasket cover that is opposite the substrate, said sample well assembly further comprising a plurality of sample wells that receive one or more DNA or RNA samples and that communicate the DNA or RNA samples to the hybridization chambers through the gasket cover; and a valve plate having a plurality of preexisting channels extending through the valve plate where a bottom of each sample well of the sample well assembly is in direct contact with a top of the valve plate, the valve plate being moveably disposed between the sample well assembly and the gasket cover in which the valve plate has a first position relative to the sample well assembly and gasket cover where each of the plurality of channels of the valve plate completes a passageway between the respective hybridization chambers and sample wells that allows the communication of the DNA or RNA samples from the sample wells to the respective hybridization chambers and a second position relative to the sample well assembly and gasket cover where a body of the valve plate blocks the passageways and isolates the sample wells from the hybridization chambers.

26. The disposable sample processing module as in claim 25 wherein the substrate further comprises a silicon glass.

27. The disposable sample processing module as in claim 26 wherein the silicon glass substrate is adapted to contact an external heating or cooling source.

28. The disposable sample processing module as in claim 25 wherein the flexible gasket further comprises silicone.

29. The disposable sample processing module as in claim 25 wherein at least some hybridization chambers of the plurality of hybridization chambers further comprise a volume of from 5 to 20 microliters.

30. The disposable sample processing module as in claim 25 wherein at least some hybridization chambers of the plurality of hybridization chambers further comprise an oligonucleotide covalently bonded to an internal surface.

31. The disposable sample processing module as in claim 25 wherein the valve plate further comprises polycarbonate.

32. The disposable sample processing module as in claim 31 wherein the polycarbonate valve plate further comprises an overmolded inert layer of silicone where the DNA or RNA samples contact the valve plate.

33. The disposable sample processing module as in claim 25 further comprising a pumping plate disposed adjacent the sample well on a side of the sample well that is opposite the gasket cover, said pumping plate further comprising a plurality of pumping ports that communicate fluids into and out of the processing module.

34. The disposable sample processing module as in claim 33 wherein the pumping plate further comprises polycarbonate.

35. The disposable sample processing module as in claim 33 wherein the plurality of pumping ports further comprise at least one waste port and a waste channel that connects the waste port with a respective hybridization chamber of the plurality of hybridization chambers.

36. The disposable sample processing module as in claim 35 wherein the waste channel further comprises a passageway through the valve plate that is blocked when the valve plate is in the second position.

37. The disposable sample processing module as in claim 35 wherein the plurality of pumping ports further comprise at least a first fluid fill port that directs fluid to each sample well of the plurality of sample wells.

38. The disposable sample processing module as in claim 37 further comprising a nozzle plate disposed between the pumping plate and the sample well, said nozzle plate having a plurality of nozzles that correspond to the plurality of sample wells and wherein a fluid introduced through the pumping nozzle is sprayed into a sample well of the plurality of sample wells through a respective nozzle of the plurality of nozzles.

39. The disposable sample processing module as in claim 38 wherein each nozzle of the plurality of nozzles further comprises a diameter of approximately 200 microns.

40. The disposable sample processing module as in claim 39 wherein the fluid sprayed through the nozzles further comprises approximately 200 microliters per second.

41. The disposable sample processing module as in claim 38 further comprising a second fluid fill port of the plurality of pumping ports, said second fluid fill port communicating with said first fluid fill port.

42. The disposable sample processing module as in claim 41 wherein the nozzle plate further comprising a microfluidics mixing chamber that mixes fluids from the first and second fluid fill ports before the mixed fluids are introduced into the plurality of sample wells.

43. The disposable sample processing module as in claim 25 wherein the sample well assembly further comprises a metal body adapted to interact with an external heater to denature the DNA or RNA samples.

44. The disposable sample processing module as in claim 43 wherein the metal body further comprises a relatively thin coating of silicone within each sample well of the plurality of sample wells to isolate the DNA or RNA samples from the metal body.

* * * * *